United States Patent [19]

Jurd

[11] 3,968,234

[45] July 6, 1976

[54] CINNAMYL-SESAMOL DERIVATIVES AS INSECT CHEMOSTERILANTS

[75] Inventor: Leonard Jurd, Berkeley, Calif.

[73] Assignee: The United States of America as represented by the Secretary of Agriculture, Washington, D.C.

[22] Filed: Mar. 5, 1975

[21] Appl. No.: 555,488

[52] U.S. Cl............................ 424/282; 260/240 D; 424/DIG. 12
[51] Int. Cl.² ................... A01N 9/28; C07D 317/06
[58] Field of Search.................. 260/240 D; 424/282

[56] References Cited
UNITED STATES PATENTS 3,686,222   8/1972   Chodnekar et al. ................. 424/282
3,723,467   3/1973   Siddall et al. ........................ 424/282

OTHER PUBLICATIONS

Borkovec, "Insect Chemosterilants," vol. VII, (1966), pp. 61–63.

*Primary Examiner*—V. D. Turner
*Attorney, Agent, or Firm*—M. Howard Silverstein; David G. McConnell; William Takacs

[57] ABSTRACT

New cinnamyl-sesamol derivatives, for example, 3,4-methylenedioxy-cinnamyloxybenzene, 2-methoxy-4,5-methylenedioxycinnamylbenzene, 2-ethoxy-4,5-methylenedioxy-cinnamylbenzene, and 2-allyloxy-4,5-methylenedioxy-cinnamylbenzene are useful for insect control, particularly as insect chemosterilants.

18 Claims, No Drawings

CINNAMYL-SESAMOL DERIVATIVES AS INSECT CHEMOSTERILANTS

DESCRIPTION OF THE INVENTION

This invention relates to and has among its objects the provision of novel cinnamyl-sesamol derivatives and the use thereof in insect control, particularly as chemosterilants for insects. Further objects of the invention will be evident from the following description wherein parts and percentages are by weight unless otherwise specified.

The abbreviation ppm used herein refers to parts per million. The symbol $\phi$ is used herein to represent the phenyl

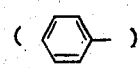

group.

One aspect of the invention concerns the provision of new organic compounds. These compounds fall into three distinct categories as follows:

I. The compound 3,4-methylenedioxy-cinnamyloxybenzene, which has the structure

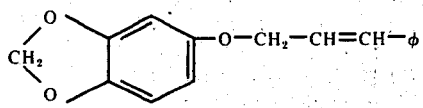

II. 2-Alkoxy-4,5-methylenedioxy-cinnamylbenzenes, which have the structure

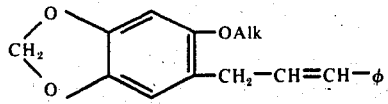

wherein Alk is an alkyl group containing 1 to 4 carbon atoms.

III. 2-Alkenyloxy-4,5-methylenedioxy-cinnamylbenzenes, which have the structure

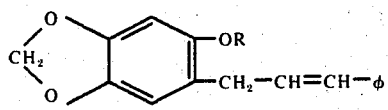

wherein R is an alkenyl group containing 2 to 4 carbon atoms, such as vinyl, allyl, methallyl, isopropenyl, or the like.

The compound of Category I may be prepared by reacting sesamol (also known as 3,4-methylenedioxyphenol) with cinnamyl chloride in the presence of a base such as potassium carbonate to convert the hydroxy group of sesamol to a cinnamyloxy group ($-O-CH_2-CH = CH-\phi$).

The compounds of Category II may be prepared in the following manner: A mixture of sesamol and cinnamyl alcohol in aqueous formic acid is refluxed to yield 2-hydroxy-4,5-methylenedioxy-cinnamylbenzene. This intermediate is then etherified in conventional manner by reaction with an appropriate alkyl halide or alkyl sulphate to yield the desired compound. The synthesis is illustrated by the following formulas.

sesamol 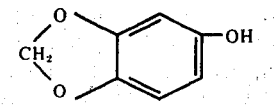

+ cinnamyl alcohol    $\phi-CH=CH-CH_2-OH$

↓ aq. formic acid 2-hydroxy-4,5-methylenedioxy-cinnamylbenzene 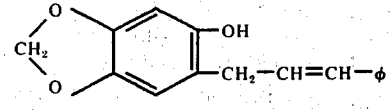

+ alkyl bromide    Alk—Br

↓ base 2-alkoxy-4,5-methylenedioxy-cinnamylbenzene 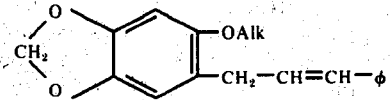

(wherein Alk is as previously defined)

The compounds of Category III may be prepared in the same manner as those of Category II, except that in the second step an alkenyl halide--such as allyl bromide--is used in place of the alkyl halide.

USE OF THE NEW COMPOUNDS

The introduction of sterilized insects into breeding centers is an effective means of biologically controlling insect populations. The sexually sterilized insects mate with fertile insects, but the union does not produce any progeny. The result in a decrease in population of the insects. This method of insect control offers many advantages over the usual method of applying an insecticide to insects or their habitat. For example, it avoids harm to humans, animals, and useful insects (bees, for instance).

In controlling insects by sterilization, a suitable sterilant is administered to a group of insects and these are then released in a locus where insects of the same species are present. As noted above, the sterile insects mate with fertile ones but without producing progeny so that the overall population is decreased.

It has been found that the compounds of the invention are useful as insect sterilants and thus can be used in the above-described method of biological insect control. Thus in a practice of this phase of the invention, insects are rendered sexually sterile by administering to them any of the compounds heretofore described. The so-treated sterile insects are then ready for release in insect breeding areas for mating with fertile insects of the same species. The administration of the compounds may be carried out by feeding the insects on a conventional insect food to which is added any of the aforesaid compounds in a concentration which is sufficient to induce sterility in the insects, but is insufficient to kill them. The concentration required to achieve sterility will vary depending on such factors as the kind of insect and the activity of the selected sterilant. In any particular case the appropriate amount to use can readily be determined by pilot tests well-known to entomologists. The sterilants of the invention can be administered to captive insects in cages or other suitable containers. Alternatively, the sterilants may be administered to wild insects, for example, by making available to them feeding stations provided with insect food admixed with any of the sterilants in sterilizing proportion.

EXAMPLES

The invention is further demonstrated by the following illustrative examples.

EXAMPLE 1

Preparation of
3,4-methylenedioxy-cinnamyloxybenzene (MDCB)

A mixture of sesamol (27.6 g.), cinnamyl chloride (30.4 g.), anhydrous potassium carbonate (50.0 g.), potassium iodide (2.0 g.) in anhydrous acetone (100 ml.) was heated under reflux for 1.5 hrs. The acetone was removed by evaporation, and the residue was treated with excess water and cooled to give an oil, which subsequently solidified. The crude product was collected by filtration and recrystallized from methanol to give MDCB as colorless prisms, m.p. 83° C., yield 15.0 g. (Found: C, 75.4; H, 5.67. Calculated for $C_{16}H_{14}O_3$: C, 75.6; H, 5.55.) The nuclear magnetic resonance (NMR) spectrum of MDCB at 100 MHz in deuterated chloroform ($CDCl_3$) exhibited absorbances as follows: a doublet (2 protons) at $\delta$ 4.59 (coupling constant J = 6.0 Hz), a singlet (2 protons) at $\delta$ 5.89 a multiplet (5 protons) at $\delta$ 6.22–6.80, and a multiplet (5 protons) at $\delta$ 7.18–7.48.

EXAMPLE 2

Preparation of
2-methoxy-4,5-methylenedioxy-cinnamylbenzene
(MMCB)

A. Preparation of intermediate, 2-hydroxy-4,5-methylenedioxy-cinnamylbenzene: Cinnamyl alcohol (100 g.) was added in portions to a warm solution of sesamol (104 g.) in formic acid (300 ml.) and water (100 ml.). The mixture was boiled under reflux for 40 min. Excess of water was added and the oily product was dissolved in boiling methanol (400 ml.). This solution was cooled and the crystals which formed were separated and discarded. The solution was evaporated and distilled to give an oil, b.p. 210°–230° C/1.0 mm. (116 g.). This partially crystallized from ether-Skellysolve F to give 60 g. of cream-colored crystals. (Skellysolve F is a petroleum hydrocarbon fraction boiling from 30° to 60° C). Recrystallization from benzene-Skellysolve F yielded 2-hydroxy-4,5-methylenedioxy-cinnamylbenzene as colorless, glistening prisms, m.p. 83° C. Found: C, 75.7; H, 5.99. Calc. for $C_{16}H_{14}O_3$: C, 75.6; H, 5.55% 100 MHz NMR spectrum in $CDCl_3$: a doublet (2 protons) at $\delta$ 3.43 (J = 6.0 Hz), a singlet (1 proton) at $\delta$ 4.87, a singlet (2 protons) at $\delta$ 5.86, a multiplet (1 proton) at $\delta$ 6.28, a singlet (1 proton) at $\delta$ 6.41, a doublet (1 proton) at $\delta$ 6.48, a singlet (1 proton) at $\delta$ 6.64, and a multiplet (5 protons) at $\delta$ 7.14–$\delta$ 7.32.

B. Preparation of final product, 2-methoxy-4,5-methylenedioxy-cinnamylbenzene (MMCB): A mixture of 19 g. of 2-hydroxy-4,5-methylenedioxy-cinnamylbenzene, 18.9 g. of dimethyl sulfate, 30.0 g. of anhydrous potassium carbonate, and 200 ml. of acetone was refluxed for 2 hrs. The mixture was then concentrated, diluted with 1% aqueous sodium hydroxide (200 ml.), and cooled. The oil which formed was extracted with ethyl ether. The ether was removed by evaporation and the residue was distilled to give MMCB (17.5 g.), b.p. 180° C at 0.25 mm. (Found: C, 75.9; H, 5.94. Calc. for $C_{17}H_{16}O_3$: C, 76.1; H, 6.01). The 100 Hz NMR spectrum of MMCB in deuterated chloroform exhibited a doublet (2 protons) at $\delta$ 3.44 (J = 6.0 Hz), a singlet (3 protons) at $\delta$ 3.74, a singlet (2 protons) at $\delta$ 5.85, a multiplet (2 protons) at $\delta$ 6.13–6.37, a singlet (1 proton) at $\delta$ 6.51, a singlet (1 proton) at $\delta$ 6.68, and a multiplet (5 protons) at $\delta$ 7.10–7.40.

EXAMPLE 3

Preparation of
2-ethoxy-4,5-methylenedioxy-cinnamylbenzene
(EMCB)

The method outlined in Example 2 was employed except that in Part B diethyl sulfate was used in place of dimethyl sulfate.

EMCB had a b.p. 197°–198° at 1.0 mm. and its 100 MHz NMR spectrum in deuterated chloroform exhibited a triplet (3 protons) at $\delta$ 1.32 (J = 7.0 Hz), a doublet (2 protons) at $\delta$ 3.43 (J = 6.0 Hz), a quartet (2 protons) at $\delta$ 3.88 (J = 7.0 Hz), a singlet (2 protons) $\delta$ at $\delta$ 5.78, a multiplet (2 protons) at $\delta$ 6.10–6.40, a singlet (1 proton) at $\delta$ 6.46, a singlet (1 proton) at $\delta$ 6.66, and a multiplet (5 protons) at $\delta$ 7.00–7.40.

EXAMPLE 4

Preparation of
2-allyloxy-4,5-methylenedioxy-cinnamylbenzene
(AMCB)

The method outlined in Example 2 was employed except that in Part B allyl bromide was used in place of dimethyl sulfate.

AMCB was a yellow oil, b.p. 100° C at 0.25 mm. Its 100 MHz NMR spectrum in deuterated chloroform exhibited a doublet (2 protons) at $\delta$ 3.45 (J = 6.0 Hz), a sextet (2 protons) at $\delta$ 4.41, a multiplet (2 protons) at $\delta$ 5.10–5.40, a singlet (2 protons) at $\delta$ 5.80, a multiplet (1 proton) at $\delta$ 5.80–6.20, a multiplet (2 protons) at $\delta$ 6.24–6.40, a singlet (1 proton) at δ 6.48, a singlet (1 proton) at δ 6.67, and a multiplet (5 protons) at δ 7.03–7.40.

EXAMPLE 5

Sterility Tests

These experiments concern testing of the compounds of the invention for inducing sterility in house flies (Musca domestica).

The compounds were administered in a standard fly food containing 6 parts of sugar, 6 parts of powdered non-fat dry milk, and 1 part of powdered egg yolk. Treated food was prepared by mixing an appropriate amount of a solution or suspension of the candidate compound in acetone with a batch of the food. The acetone was evaporated (4–6 hrs.) and the dry material was repulverized.

Preliminary tests: Samples of treated food with a container of water was placed in cages containing 100 newly-emerged adult flies. After the flies had been exposed to the treated diet for 6–7 days, ½ inch of moist standard fly larva rearing medium (CSMA) in souffle cups was placed in the cages for oviposition. After 4–6 hrs. the cups were filled with water and stirred to break up the egg masses. A random sample of 100 eggs from each cup was collected and placed on a small piece of black cloth which was then laid on top of moist larva-rearing medium in a rearing container. Observations were made to determine percentage of egg hatch and pupal development.

Cross-breeding tests: In those cases where the preliminary tests indicated that sterility had occurred in the flies fed the treated food, 10 males were removed from the test cage and crossed with 10 virgin, 4-day old, untreated females. These flies were maintained on untreated fly food. After 5 days, cups containing the larval-rearing medium were provided as previously described and a 100-egg sample was collected and placed on moist larva-rearing medium. About a week after oviposition examination was made to determine the percentage of hatched eggs and of pupae developed. The results of these cross-breeding experiments are summarized below.

| Sterilant used | Amount of sterilant in food, % | Mortality (parent generation) % | Egg hatch, % | Pupal development % |
|---|---|---|---|---|
| MDCB | 0.25 | 0 | 2 | 2 |
| '' | 0.50 | 0 | 5 | 5 |
| MMCB | 0.05 | 0 | 39 | 39 |
| '' | 0.1 | 0 | 9 | 3 |
| AMCB | 0.25 | 0 | 0 | 0 |
| None | 0 | 0 | 92–93 | 92–93 |

For purpose of comparison the above described tests were applied to 2-hydroxy-4,5-methylenedioxy-cinnamylbenzene at a concentration of 1% in the fly food. The tests demonstrated that this compound was ineffective to induce sexual sterility.

Having thus described the invention, what is claimed is:

1. The compound of the structure

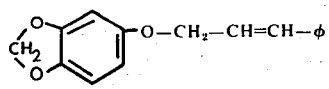

2. A compound of the structure

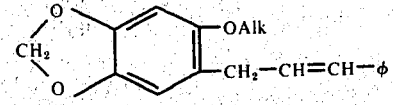

wherein Alk is an alkyl radical containing 1 to 4 carbon atoms.

3. The compound of claim 2 wherein Alk is methyl
4. The compound of claim 2 wherein Alk is ethyl.
5. A compound of the structure

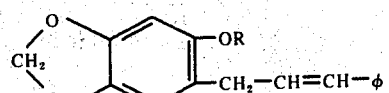

wherein R is an alkenyl group containing 2 to 4 carbon atoms.

6. The compound of claim 5 wherein R is allyl.
7. A composition for inducing sexual sterility in flies consisting essentially of
   a. a fly food, and
   b. 3,4-methylenedioxy-cinnamyloxybenzene in an amount insufficient to kill flies which ingest the composition but sufficient to induce sexual sterility therein.
8. A composition for inducing sexual sterility in flies consisting essentially of
   a. a fly food, and
   b. a compound of the structure

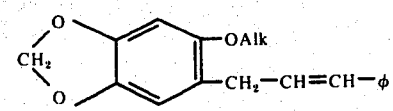

wherein Alk is an alkyl radical containing 1 to 4 carbon atoms,
   said compound being in an amount insufficient to kill flies which ingest the composition but sufficient to induce sexual sterility therein.

9. The composition of claim 8 wherein Alk is methyl.
10. The composition of claim 8 wherein Alk is ethyl.
11. A composition for inducing sexual sterility in flies consisting essentially of
    a. a fly food, and
    b. a compound of the structure

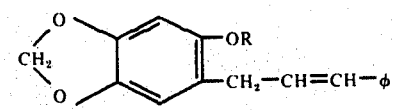

wherein R is an alkenyl radical containing 2 to 4 carbon atoms, said compound being in an amount insufficient to kill flies which ingest the composition but sufficient to induce sexual sterility therein.

12. The composition of claim 11 wherein R is allyl.

13. A method of causing sterility in flies, which comprises
providing for ingestion by the flies a food containing the compound 3,4-methylenedioxy-cinnamyloxy-benzene in an amount insufficient to kill the flies but sufficient to induce sexual sterility therein.

14. A method of causing sexual sterility in flies, which comprises
providing for ingestion by the flies a food containing a compound of the structure

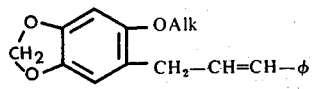

wherein Alk is an alkyl radical containing 1 to 4 carbon atoms, in an amount insufficient to kill the flies but sufficient to induce sexual sterility therein.

15. The method of claim 14 wherein Alk is methyl.

16. The method of claim 14 wherein Alk is ethyl.

17. A method of causing sexual sterility in flies, which comprises
providing for ingestion by the flies a food containing a compound of the structure

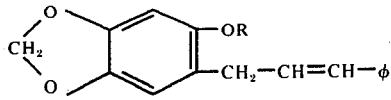

wherein R is an alkenyl radical containing 2 to 4 carbon atoms, in an amount insufficient to kill the flies but sufficient to induce sexual sterility therein.

18. The method of claim 17 wherein R is allyl.

* * * * *